United States Patent [19]
Poetsch et al.

[11] Patent Number: 5,817,862
[45] Date of Patent: Oct. 6, 1998

[54] PROCESS FOR THE PREPARATION OF CINNAMIC ACID DERIVATIVES

[75] Inventors: Eike Poetsch, Mühltal; Volker Meyer, Groβ-Zimmern; Ulrich Heywang, Darmstadt; Rainer Christ, Frankfurt; Jürgen Seubert, Darmstadt, all of Germany

[73] Assignee: Merck Patent Gesellschaft mit Beschrankter Haftung, Germany

[21] Appl. No.: 702,471

[22] PCT Filed: Feb. 7, 1995

[86] PCT No.: PCT/EP95/00428

§ 371 Date: Aug. 22, 1996

§ 102(e) Date: Aug. 22, 1996

[87] PCT Pub. No.: WO95/23126

PCT Pub. Date: Aug. 31, 1995

[30] Foreign Application Priority Data

Feb. 23, 1994 [DE] Germany .......................... 44 05 830.6

[51] Int. Cl.$^6$ .............................. C07C 69/76; C07C 63/64
[52] U.S. Cl. .............................. 560/104; 560/47; 560/55; 560/64; 560/65; 560/76; 562/452; 562/465; 562/495
[58] Field of Search .................................. 560/55, 47, 64, 560/65, 76, 104; 562/452, 465, 495

[56] References Cited

PUBLICATIONS

Chemical Abstracts 116: 58980 CA 1991.

*Primary Examiner*—Paul J. Killos
*Attorney, Agent, or Firm*—Millen, White, Zelano & Branigan, P.C.

[57] ABSTRACT

The invention relates to a process for the preparation of cinnamic acid derivatives which involves reacting chlorinated aromatic compounds and acrylic acid derivatives in the presence of palladium catalysts.

16 Claims, No Drawings

PROCESS FOR THE PREPARATION OF CINNAMIC ACID DERIVATIVES

The present invention relates to a process for the preparation of cinnamic acid derivatives.

It is already known that olefins can be arylated by bromoaromatic compounds in the presence of palladium catalysts, phosphine ligands and a base (see R. F. Heck, Org. React. 27, 345–391 (1982)).

According to Y. Ben-David et al., Organometallics 11, 1995 (1992) the arylation of alkenes using chloro-aromatic compounds can only be carried out in the presence of bidentate phosphine ligands.

The reaction is frequently carried out with various amines (e.g. triethylamine, tributylamine, tetramethylethylenediamine), which may serve simultaneously as solvent. The bases employed may include alkali metal carboxylates in dimethylformamide (see EP-A 78 768) or alkali metal carbonates or hydrogen carbonates, given the simultaneous presence of a polar aprotic solvent (e.g. dimethylformamide, hexamethylphosphoric triamide, acetonitrile) and a phase transfer catalyst (see Tetrahedron Lett. 26, 2667–2670 (1985) and J. Org. Chem. 56, 1289–1293 (1991)).

Furthermore, the patent application WO 90/10617 discloses that, in a two-step process, p-methoxyaniline (=p-anisidine) can first of all be diazotized, and then the product can be converted using potassium iodide into 4-iodanisole. This product can subsequently be reacted with 2-ethylhexyl acrylate, in the presence of triethylamine and a palladium catalyst, to give 2-ethylhexyl 4-methoxycinnamate. This process involves a large number of steps and requires the recovery of alkali metal iodide.

The reaction of 4-iodoanisole with methyl acrylate and a stoichiometric quantity of tetramethyl-ethylenediamine in the presence of 1 mol% of palladium(II) acetate results, after 5 hours at 100° C., in a yield of only 68% of methyl 4-methoxycinnamate (J. Org. Chem. 37, 2320–2322 (1972)).

The reaction of 4-bromoanisole with methyl acrylate and a stoichiometric quantity of tetramethyl-ethylenediamine in the presence of from 1 to 2 mol% of palladium(II) acetate and 2 to 4 mol% of triphenyl-phosphine gives, after 36 hours at 135° C., a yield of methyl 4-methoxycinnamate of 54% (J. Am. Chem. Soc. 96, 1133–1136 (1974)).

DE 42 11 608 proposes the reaction of bromoaromatic compounds with acrylic acid derivatives in the presence of palladium catalysts and a large excess of phosphines, based on palladium. The phosphine produced in relatively large quantities in this reaction creates additional difficulties in isolating the product.

EP 0 509 426 describes the preparation of octyl p-methoxycinnamate from p-bromoanisole and octyl acrylate in the presence of a base and of a coupling catalyst in a polar aprotic solvent. All of the processes which have been disclosed to date produce bromide salts as by-products, resulting in a considerable pollution of the waste water or in a laborious recovery procedure. None of the processes known to date has a successful outcome with the corresponding chlorine derivative.

EP 103 544 describes a process for the arylation of acrylonitrile with p-chlorobenzaldehyde in the presence of chloro(4-formylphenyl)bis(triphenyl-phosphine)palladium (II), the product being obtained in a yield of only 18%.

There is therefore a need for a process which can be used to react the chloroaromatic compounds, which are less reactive but easier to prepare, in the presence of palladium catalysts with acrylic acid derivatives in high space-time yields and without the use of auxiliaries requiring any particular complexity.

A process has now been found for the preparation of cinnamic acid derivatives from chloroaromatic compounds and acrylic acid derivatives in the presence of palladium catalysts and a phosphine, which process is characterized in that a lipophilic, aliphatic phosphine is employed of the formula I $$\begin{array}{c} R^1 \\ \diagdown \\ P-R^2 \\ \diagup \\ R^1 \end{array} \qquad (I)$$

in which $R^1$ at each occurrence independently of one another is straight-chain or branched $C_{1-6}$-alkyl, $C_{1-6}$-alkoxy, $C_{4-8}$-cycloalkyl or $C_{4-8}$-cycloalkoxy, preferably branched $C_{3-6}$-alkyl, $C_{3-6}$-alkoxy or cyclohexyl, and $R^2$ is straight-chain or branched $C_{1-6}$-alkyl, $C_{1-6}$-alkoxy, $C_{4-8}$-cycloalkyl or $C_{4-8}$-cycloalkoxy or a radical of the formula II $$\begin{array}{c} R^1 \\ \diagup \\ -R^3-P \\ \diagdown \\ R^1 \end{array} \qquad (II)$$

in which $R^3$ is divalent $C_{1-20}$-alkylene, and $R^1$ is as defined above.

The quantity of palladium can be chosen such that, based on the chloroaromatic compound employed, its proportion is from 0.0001 to 1 mol%, preferably from 0.005 to 0.05 mol%.

The acrylic acid derivatives employed may, for example, be those of the formula (III):

$$\begin{array}{c} R' \\ | \\ \diagup\!\!\!\diagdown_R \end{array} \qquad (III)$$

in which

R is CN or $COR^4$, where $R^4$ is OH, $O-C_6-C_{10}$-aryl, $O-C_1-C_{20}$-alkyl, $NH_2$, $NH-C_6-C_{10}$-aryl, $NH-C_1-C_{20}$-alkyl, $N-C_6-C_{10}$-aryl, $N-C_1-C_{20}$-alkyl-$C_6-C_{10}$-aryl or $N$-di-$C_1-C_{20}$-alkyl, and R' is H, $C_1-C_{20}$-alkyl, $C_6-C_{20}$-aryl or R.

In the formula (III) R is preferably $COR^4$ with $R^4=O-C_1-C_{20}$-alkyl, particularly preferably $O-C_1-C_{10}$-alkyl and, in particular, 2-ethylhexyloxy. Chloroaromatic compounds which can be employed are, for example, chlorobenzenes of the formula (IV)

$$(Cl)_m \underset{Cl}{\underset{|}{\bigcirc}} (R^5)_n \qquad (IV)$$

in which $R^5$ is $C_6-C_{10}$-aryl, $C_{1-20}$-alkyl, CN, $S-R^6$, $CO-OR^6$, $-F$, $-OCF_3$, $OR^6$ or $NR^6_2$ where $R^6$ is hydrogen, $C_6-C_{10}$-aryl or $C_{1-20}$-alkyl, m is 0 or 1, n is 1 to 5, and n+m is 1 to 5.

In the formula (IV) $R^5$ is preferably $OR^6$ or $NR^6_2$ where $R^6$=phenyl or $C_{1-10}$-alkyl; $R^5$ is particularly preferably methoxy. m is preferably 0, and n is preferably 1.

The molar ratio of chloroaromatic compound to acrylic acid derivative can be chosen as desired. Preference is given to working at a molar ratio of chloroaromatic compound to acrylic acid derivative which is in the range from 1:0.7 to 1:3. With particular preference this ratio is from 1:0.8 to 1:1.5.

Generally, in the case of dichlorobenzene derivatives (m=1), double the quantity of acrylic acid derivative is employed.

Suitable inorganic bases for the process according to the invention are, for example, alkali metal and alkaline earth metal salts of weak acids, preferably alkali metal and alkaline earth metal hydrogen carbonates and/or carbonates. Particular preference is given to the use of sodium carbonate. The ratio of chloroaromatic compound to base is preferably chosen such that from 0.3 to 2, particularly preferably from 0.4 to 1.3, equivalents of base are employed per mole of chloroaromatic compound.

The lipophilic, aliphatic phosphine ligands of the formula I are obtainable commercially or can be prepared in analogy to processes which are known per se.

In the preferred monodentate phosphine ligands of formula I the radicals $R^1$ and $R^2$ are identical and have a branched alkyl or alkoxy group or a cyclohexyl group.

Accordingly, preferred monodentate phosphine ligands are: trimethylphosphine, triethylphosphine, tripropylphosphine, triisopropylphosphine, tributylphosphine, tricyclohexylphosphine, trimethyl phosphite, tripropyl phosphite, triisopropyl phosphite, tributyl phosphite and tricyclohexyl phosphite, in particular triisopropylphosphine or tricyclohexylphosphine.

In the preferred bidentate phosphine ligands of formula (I) the radicals $R^1$ are in each case identical, and $R^2$ is a radical of formula (II) in which $R^3$ is preferably divalent $C_{2-6}$-alkylene.

Accordingly, preferred bidentate phosphine ligands are: 1,2-bis(dimethylphosphine)ethane, 1,2-bis(diethylphosphine)ethane, 1,2-bis(dipropylphosphine)ethane, 1,2-bis(diisopropylphosphine)ethane, 1,2-bis(dibutylphosphine)ethane, 1,2-bis(dicyclohexylphosphine)ethane, 1,3-bis(dicyclohexylphosphine)propane, 1,3-bis(diisopropylphosphine)propane, 1,4-bis(diisopropylphosphine)butane and 2,4-bis(dicyclohexylphosphine)pentane.

Phosphines can be employed in the process according to the invention, for example, in a molar ratio of palladium:phosphorus of from 1:0.8 to 1:2.5. This ratio is preferably from 1:0.9 to 1:2.3 and particularly preferably about 1:2.

It is self-evident that the ratios indicated relate to the monodentate phosphines of the formula I; in the case of the bidentate phosphines the palladium:phosphine ratios generally employed are from 1:0.4 to 1:1.25.

The process according to the invention can be carried out, for example, at temperatures in the range from 50° to 180° C. Preferred temperatures are in the range from 80° to 150° C., and with particular preference are in the region of the boiling point of the solvent employed. The process according to the invention is usually carried out at atmospheric pressure. However, it can also be carried out at reduced or elevated pressure. The application of elevated pressure is particularly appropriate when it is desired to work at a reaction temperature at which individual components of the reaction mixture would boil at atmospheric pressure.

The process according to the invention is generally carried out under a protective gas, for example nitrogen, and with stirring.

Suitable solvents are hydrocarbons such as, for example, toluene, ethers such as tetrahydrofuran, polar aprotic solvents such as, for example, N-methyl-pyrrolidone, dimethylformamide, N,N-dimethylacetonitrile or dimethyl sulfoxide.

Using the process according to the invention it is possible, for example, to prepare cinnamic acid derivatives of the formula (V)

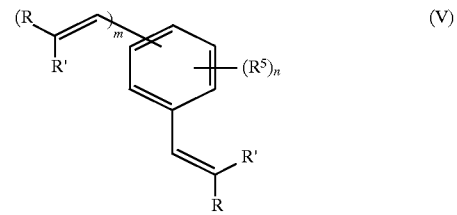

in which the symbols used have the meaning indicated in the case of the formulae (III) and (IV).

After the process according to the invention has been carried out, the inorganic salts formed can be separated off, for example, by simple filtration, with or without suction. It is also possible to leave the salts to settle and to decant the rest of the reaction mixture.

One possible embodiment of the process according to the invention is described below by way of example of the reaction of 4-chloroanisole with 2-ethylhexyl acrylate:

trialkylphosphine and palladium(II) chloride are added in a molar ratio of palladium:phosphorus of 1:2 to an initial charge of 4-chloroanisole, 2-ethylhexyl acrylate, sodium carbonate and N-methylpyrrolidone (NMP). The sequence of addition of these components can be altered as desired. The mixture is then heated at 140° to 150° C. under nitrogen and with vigorous stirring. After it has been determined that no further 4-chloroanisole is reacting, the reaction is terminated: that is, the reaction mixture is cooled to room temperature and poured into water. The aqueous phase is then separated off and extracted with an organic solvent (e.g. methyl tert.-butyl ether (MTB)). The combined extracts obtained are freed from the solvent and distilled in vacuo.

It is surprising that the palladium-catalyzed therefor reaction, according to the invention, of relatively unreactive chloroaromatic compounds with acrylic acid derivatives, with the use of very small quantities of palladium catalyst having a phosphorus ligand of the formula I, gives high space-time yields.

The process according to the invention makes it possible to prepare cinnamic acid derivatives, especially 2-ethylhexyl p-methoxycinnamate and isoamyl 4-methoxy-cinnamate, under advantageous reaction conditions, with no particular expenditure being necessary for the handling of auxiliaries (bases, solvents). The bases, solvents and phosphines required are readily accessible and inexpensive.

The process according to the invention is significantly more economical and, in comparison with the processes of the prior art, achieves a higher space-time yield.

Cinnamic acid derivatives, especially the 2-ethylhexyl and isoamyl esters of p-methoxycinnamic acid, can be employed, for example, as UV absorbers in cosmetics (see U.S. Pat. No. 5,008,100 and U.S. Pat. No. 4,810,490).

EXAMPLE 1

24.8 ml of 4-chloroanisole, 52.3 ml of 2-ethyl-hexyl acrylate, 10.6 g of sodium carbonate and 200 ml of NMP are placed in a four-necked round-bottomed flask, and 2.3 mg of tricyclohexylphosphine and 0.9 mg of palladium acetate (2.0 mol% based on 4-chloroanisole) were added. The mixture was heated at 140°–150° C. under nitrogen and with stirring. After 60 hours the conversion according to gas chromatography was 68%, based on the 4-chloroanisole employed.

The mixture is cooled and poured into water. After extraction with 3×200 ml of MTB ether, the organic phase formed by combination of the extracts is washed with water, dried over sodium sulfate and filtered. After removal of the solvent the filtrate is distilled under reduced pressure. The yield of isolated 2-ethylhexyl p-methoxycinnamate is 14.5 g.

EXAMPLE 2 (COMPARISON EXAMPLE)

The procedure of Example 1 was followed, but adding 2.1 g of triphenylphosphine. After 60 hours the conversion according to gas chromatography was 0.5%, based on the 4-chloroanisole employed.

EXAMPLE 3

The procedure of Example 1 was followed, but adding 1.5 mg of triisopropylphosphine instead of tricyclohexylphosphine. After 60 hours the conversion according to gas chromatography was 65%, based on the 4-chloroanisole employed.

We claim:

1. A process for the preparation of a cinnamic acid compound which comprises reacting a chloroaromatic compound and an acrylic acid compound in the present of a palladium catalyst and a phosphine, wherein the phosphine is a lipophilic, aliphatic phosphine of the formula I

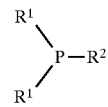
(I)

in which $R^1$ at each occurrence independently of one another is straight-chain or branched $C_{1-6}$-alkyl, $C_{1-6}$-alkoxy, $C_{4-8}$-cycloalkyl or $C_{4-8}$-cycloalkoxy, $R^2$ is straight-chain or branched $C_{1-6}$-alkyl, $C_{1-6}$-alkoxy, $C_{4-8}$-cycloalkyl or $C_{4-8}$-cycloalkoxy or a radical of the formula II

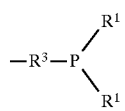
(II)

in which $R^3$ is divalent $C_{1-20}$-alkylene, and $R^1$ is as defined above.

2. A process according to claim 1, wherein the palladium catalyst is a palladium compound in oxidation state 0 and/or +2 and is present in the reaction in a quantity of from 0.0001 to 1 mol% of palladium based on chloroaromatic compound.

3. A process according to claim 1, wherein the acrylic acid compound is of the formula (III)

(III)

in which

R is CN or $COR^4$, wherein $R^4$ is OH, O—$C_6$—$C_{10}$-aryl, O—$C_1$—$C_{20}$-alkyl, $NH_2$, NH—$C_6$—$C_{10}$-aryl, NH—$C_1$—$C_{20}$-alkyl, N—$C_6$—$C_{10}$-aryl, N—$C_1$—$C_{20}$-alkyl-$C_6$—$C_{10}$-aryl or N-di-$C_1$—$C_{20}$-alkyl, and R' is H, $C_1$—$C_{10}$-alkyl, $C_6$—$C_{20}$-aryl or R.

4. A process according to claim 1, wherein the chloroaromatic compound is a chlorobenzene of the formula

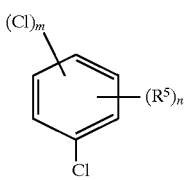

in which $R^5$ is $C_6$—$C_{10}$-aryl, $C_{1-20}$-alkyl, CN, S—$R^6$, CO—$OR^6$, —F, —$OCF_3$, $OR^6$ or $NR^6_2$ where $R^6$ is hydrogen, $C_6$—$C_{10}$-aryl or $C_{1-20}$-alkyl, m is 0 or 1, n is 1 to 5, and n+m is 1 to 5, and a molar ratio of chloroaromatic compound to acrylic acid compound is in the range from 1:0.7 to 1:3.

5. A process according to claim 1, wherein the reaction is carried out at temperatures in the range from 50° to 180° C.

6. A process according to claim 1, wherein the reaction is carried out under a protective gas and with stirring.

7. The process of claim 1, wherein each $R^1$ is independently branched $C_{3-6}$-alkyl, $C_{3-6}$-alkoxy or cyclohexyl.

8. The process of claim 3, wherein R in formula (III) is $COR^4$ where $R^4$ is O—$C_1$—$C_{20}$-alkyl.

9. The process of claim 4, wherein $R^5$ in formula (IV) is $OR^6$ or $NR^6$ where $R^6$ is phenyl or $C_{1-10}$-alkyl, m is 0 and n is 1.

10. The process of claim 1, wherein each of the $R^1$ radicals and the $R^2$ radical are identical and contain a branched alkyl or alkoxy group or a cyclohexyl group.

11. The process of claim 1, wherein the radicals $R^1$ are identical and $R^2$ is a radical of the formula (II) where $R_3$ is $C_{2-6}$-alkylene.

12. The process of claim 1, wherein the molar ratio of palladium:phosphine is from 1:0.8 to 1:2.5.

13. The process of claim 1, wherein the $R^2$ is a radical of the formula (II) and the molar ratio of palladium:phosphine is from 1:0.4 to 1:1.25.

14. The process of claim 1, wherein the cinnamic acid compound prepared is 2-ethylhexyl p-methoxycinnamate or isoamyl 4-methoxycinnamate.

15. The process of claim 1, wherein the reaction is carried out at a temperature in the range of 80° to 150° C.

16. The process of claim 1, wherein the reaction is conducted in the presence of a solvent.

* * * * *